United States Patent [19]
Weintraub et al.

[11] Patent Number: 5,990,328
[45] Date of Patent: Nov. 23, 1999

[54] PROCESS FOR THE PREPARATION OF 4-AMINO-Δ4-3-KETOSTEROIDS VIA 4-NITRO-Δ4-3-KETOSTEROIDS

[75] Inventors: Philip M. Weintraub, Cincinnati; Michael R. Angelastro, Mason; Cynthia A. Gates, Fairfield, all of Ohio; Gary Alan Flynn, Tucson, Ariz.; Timothy Thomas Curran, Chester, N.Y.; Chi-Hsin Richard King, Taipei, Taiwan

[73] Assignee: Merrell Pharmaceuticals Inc., Bridgewater, N.J.

[21] Appl. No.: 09/256,353

[22] Filed: Feb. 24, 1999

Related U.S. Application Data

[62] Division of application No. 09/010,974, Jan. 22, 1998, which is a division of application No. 08/737,031, filed as application No. PCT/US95/04399, Apr. 11, 1995, Pat. No. 5,750,744, which is a continuation-in-part of application No. 08/231,433, May 2, 1994, abandoned.

[51] Int. Cl.[6] ................................................. C07J 41/00
[52] U.S. Cl. ......................................... 552/515; 552/522
[58] Field of Search ...................................... 552/515, 522

[56] References Cited

PUBLICATIONS

Ekhato et al, Synthesis of new nitro and amino sterols, J. Chem. Soc., Perkin Trans. 1, vol. 12, 3239–42, 1988.

*Primary Examiner*—Shelley A. Dodson
*Assistant Examiner*—Alton Pryor
*Attorney, Agent, or Firm*—Barbara E. Kurys

[57] ABSTRACT

The present invention provides 4-nitro-$\Delta^4$-3-ketosteroids, their use as steroid $C_{17-20}$ lyase and 5α-reductase inhibitors and to a novel process for preparing a compound of the formula:

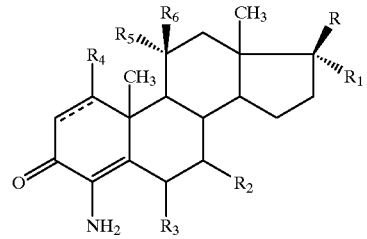

comprising sequentially:
  a) reacting a starting compound of the formula

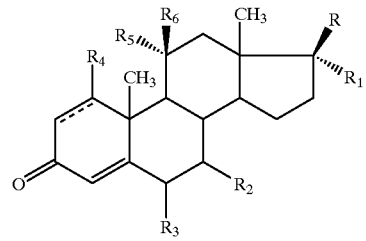

with an effective amount of a strong base at an elevated or suitable temperature for a time sufficient to create the corresponding thermodynamic dienolate, followed by addition of a neutral nitrating agent to produce the 4-nitrosteroid; and then;
  b) reacting the 4-nitrosteroid with a suitable reducing agent.

21 Claims, No Drawings

PROCESS FOR THE PREPARATION OF 4-AMINO-Δ4-3-KETOSTEROIDS VIA 4-NITRO-Δ4-3-KETOSTEROIDS

CROSS REFERENCE TO RELATED APPLICATIONS

The present application is a division of U.S. Ser. No. 09/010,974, filed Jan. 22, 1998, which is a divisional of Ser. No. 08/737,031, filed Feb. 11, 1997 now U.S. Pat. No. 5,750,744, which is a CIP of Ser. No. 08/231,433, filed May 2, 1994 now abandoned, and a U.S. Chapter 2 filing of PCT/US95/04399 which has an effective filing date of Apr. 11, 1995.

BACKGROUND OF THE INVENTION

The invention relates generally to androgenic and/or estrogenic inhibitor compounds, their use in the inhibition of $C_{17-20}$ lyase, $C_{17\alpha}$-hydroxylase and 5α-reductase, and a method for the preparation of 4-amino-Δ$^4$-3-ketosteroids.

Androgenic and estrogenic biosynthesis is principally controlled by the action of the dual acting enzyme steroid $C_{17-20}$ lyase and $C_{17\alpha}$-hydroxylase. While $C_{17-20}$ lyase catalyses the conversion of steroids having a two carbon side chain at the 17β-position, $C_{17\alpha}$-hydroxylase places a hydroxyl group of such a molecule at the 17α-position. The action of $C_{17-20}$ lyase creates important precursor molecules to the formation of testosterone, 5α-dihydrotestesterone and the estrogens, principally estrone and estradiol. Effective inhibition of $C_{17-20}$ lyase would be useful in inhibiting the formation of both androgenic and estrogenic steroids, and thus is useful in the treatment of disease states or disorders where said androgens and/or estrogens play an adverse role.

The enzyme steroid 5α-reductase catalyzes the conversion of testosterone into dihydrotestosterone or DHT (17β-hydroxy-5α-androstan-3-one). DHT is a more potent androgen than testosterone and acts as an end-organ effector in certain tissues, particularly in mediating growth. Effective inhibition of this enzyme would be useful in preventing the formation of DHT, which thus is useful in the treatment of androgen dependent disorders, particularly those in which DHT plays a principal adverse role.

As the previously mentioned inhibitors affect various steps of the androgenic and/or estrogenic pathway, each with known therapeutic utility in the treatment of various androgen and/or estrogen dependent disorders, an alternative technique for the synthesis of said inhibitors would also be useful. Certain of the 4-aminosteroid derivatives which may be obtained by the process described in this application are disclosed in U.S. Pat. No. 4,757,061, issued Jul. 12, 1988, U.S. Pat. No. 5,120,840, issued Jun. 9, 1992 and U.S. Pat. No. 5,143,909, issued Sep. 1, 1992. The disclosed three step synthesis of these compounds involves formation of a 4,5-epoxysteroid derivative followed by treatment with sodium azide to provide the 4-azidosteroid derivative. The 4-azidosteroid derivative is subsequently reduced to provide the 4-aminosteroid derivative. The use of sodium azide in this synthesis involves health risks due to the inherent instability of the compound. A skilled chemist can safely carry out the above process on a small scale in the laboratory, because only a small quantity of sodium azide is used. However, the large scale industrial production of the 4-aminosteroid derivative requires large amounts of sodium azide and its derivative acid, hydrazoic acid. This synthesis, which requires large quantities of sodium azide and hydrazoic acid at elevated temperatures poses significant risks to human life and the environment. The environmental and health risks could be reduced through appropriate design of a chemical plant, however the cost of such a facility would be prohibitive and the inherent risks could still not be entirely eliminated. The three step synthesis of a 4-amino-Δ$^4$-steroid via the 4 azido-intermediate is graphically illustrated in Scheme A.

Scheme A

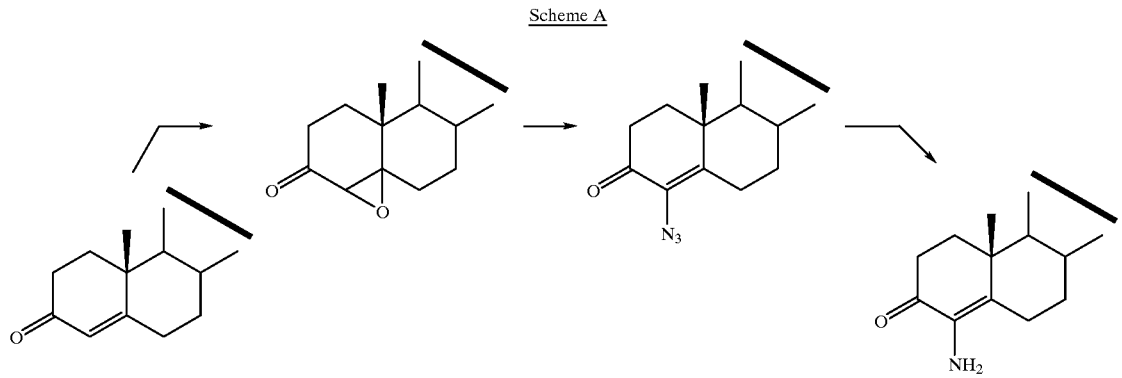

Previous attempts at nitrating Δ$^4$-3-ketosteroids, described by Schaub, et al. in *Tetrahedron* 20:373 (1964) and by Suginome et al. *J. Bull. Chem. Soc. Jap.* 62:1343 (1989), resulted in formation of the corresponding 2-nitrosteroid. This is suggested to have occurred because the nitration is effected through the kinetic 2,4-dienolate rather than the 3,5-dienolate which is the thermodynamic dienolate. The creation of 4-nitrosteroids would require conditions which are supportive to generation of a 3,5-dienolate as opposed to the 2,3-dienolate.

SUMMARY OF THE INVENTION

The present invention provides a novel process for the preparation of 4-amino-3-ketosteroids via the formation of 4-nitro-3-ketosteroids which are the product nitration of the corresponding 3,5-dienolate.

The present invention provides a novel process for preparing a compound of the formula:

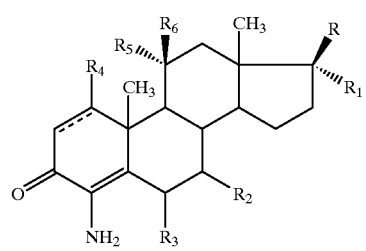

wherein

R is OH, $C_1$–$C_6$ alkanoyl, $C_1$–$C_6$ alkanoyloxy, $C_1$–$C_4$ alkanol, $COCH_2OH$, $CO_2H$, $CONR_7R_8$, cyclopropyloxy, cyclopropylamino, acetylthioalkane, 2,2-dimethyldioxolan-4-yl, 1,2-dihydroxyethyl, and $C_{1-4}$ alkanethiol;

$R_1$ is hydrogen, hydroxy or $C_{1-6}$ alkyl;

R and $R_1$ together may indicate =O, that is an oxygen double bonded to the 17 carbon;

$R_2$, $R_3$ and $R_4$ are each independently hydrogen or $C_1$–$C_6$ alkyl;

$R_5$ and $R_6$ are each independently hydrogen or OH;

$R_5$ and $R_6$ together may indicate =O, that is an oxygen double bonded to the 11 carbon;

$R^7$ is hydrogen or $C_1$–$C_8$ alkyl;

$R_8$ is $C_1$–$C_8$ alkyl; and the notation

on the ring indicates that the bond may be a single or double bond;

the notation

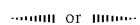

indicates a substituent in the α-configuration (below the plane of the paper);

the notation

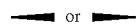

indicates a substituent in the β-configuration (above the plane of the paper);

wherein further the above is limited:

with the proviso that when R is OH, then $R_1$ is hydrogen; and with the proviso that, when $R_5$ is OH, then $R_6$ is hydrogen; comprising sequentially:

a) reacting a starting compound of the formula

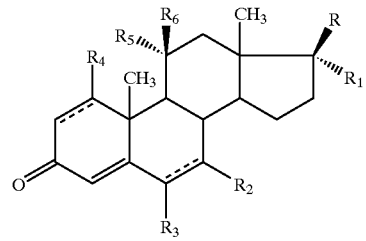

I wherein R–$R_8$ and

, and

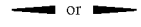

are defined as above, with an effective amount of a strong base at an elevated or suitable temperature for a time sufficient to generate the corresponding thermodynamic dienolate, followed by addition of a neutral nitrating agent to produce a 4-nitrosteroid, and then;

b) reacting the 4-nitrosteroid with a suitable reducing agent; and c) optionally converting the 4-aminosteroid into a pharmaceutically acceptable salt.

Where post nitration modifications are required these can be made in the usual manner, by known procedures. For example, oxidation of the $C_{17}$ hydroxyl group of 4-nitrotestosterone gives the corresponding 17-ketone as depicted in the following scheme:

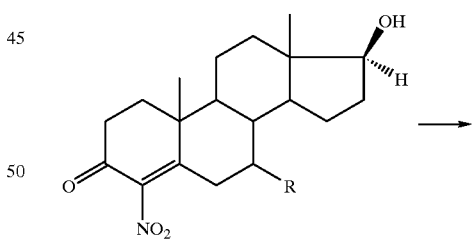

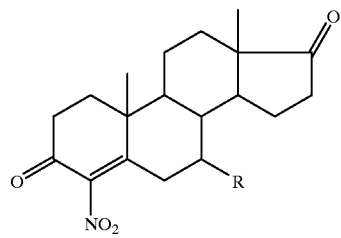

Removal of protecting groups can be effected as shown in the following scheme:

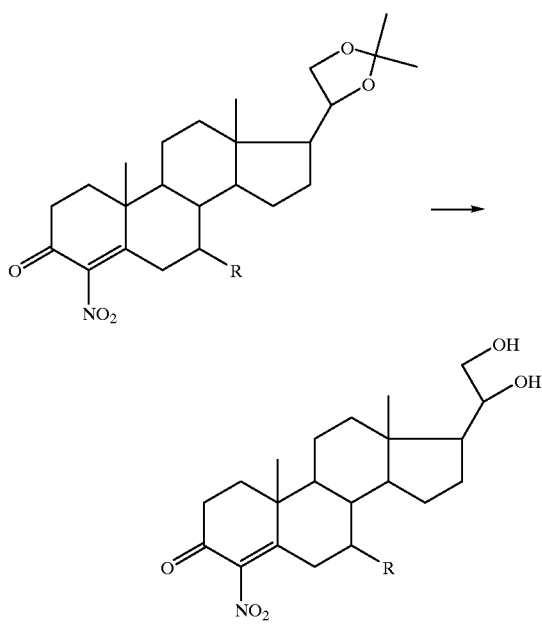

The present invention further provides certain 4-nitrosteroids which are useful as inhibitors of $C_{17\text{-}20}$ lyase, $C_{17\alpha}$-hydroxylase and/or 5α-reductase. These compounds are represented by the formula:

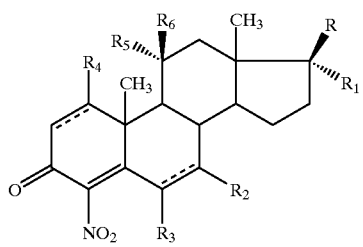

wherein

R is OH, $C_1$–$C_6$ alkanoyl, $C_1$–$C_6$ alkanoyloxy, $C_1$–$C_4$ alkanol, $COCH_2OH$, $CO_2H$, $CONR_7R_8$, cyclopropyloxy, cyclopropylamino, acetylthioalkane, 2,2-dimethyldioxolan-4-yl, 1,2-dihydroxyethyl and $C_{1\text{-}4}$ alkanethiol;

$R_1$ is hydrogen, hydroxy or $C_{1\text{-}6}$ alkyl;

R and $R_1$ together may indicate =O, that is an oxygen double bonded to the 17 carbon;

$R_2$, $R_3$ and $R_4$ are each independently hydrogen or $C_1$–$C_6$ alkyl;

$R_5$ and $R_6$ are each independently hydrogen or OH;

$R_5$ and $R_6$ together may indicate =O, that is an oxygen double bonded to the 11 carbon;

$R_7$ is hydrogen or $C_1$–$C_8$ alkyl;

$R_8$ is $C_1$–$C_8$ alkyl; and the notation

----- on the ring indicates that the bond may be a single or double bond;

the notation

........ or |||||| indicates a substituent in the α-configuration (below the plane of the paper);

the notation

◀ or ▶ indicates a substituent in the β-configuration (above the plane of the paper);

wherein further the above is limited:

with the proviso that when R is OH, then $R_1$ is hydrogen; and with the proviso that, when $R_5$ is OH, then $R_6$ is hydrogen.

The present invention further provides to a method of inhibiting steroid $C_{17\text{-}20}$ lyase, $C_{17\alpha}$-hydroxylase and/or 5α-reductase which comprising the administration of an effective inhibitory amount of the compounds of the invention.

DETAILED DESCRIPTION OF THE INVENTION

The starting compounds are known or may be obtained by known techniques.

As used herein the term "$C_1$–$C_6$ alkanoyl" refers to a straight or branched chain alkanoyl radical of from one to six carbon atoms. Included within the scope of this term are formyl, acetyl, propionyl, butyryl, isobutyryl, hexanoyl and the like.

As used herein the term "$C_1$–$C_4$ alkanol" refers to a straight or branched chain alcohol radical of from one to four carbon atoms, containing at least one hydroxy functional group, but no more than 1 hydroxy group attached to each carbon atom. Included within the scope of this term are methanol, ethanol, n-propanol, isopropanol, n-butanol, 2-butanol, 2-methyl-1-propanol, 2-methyl-2-propanol, 1,2-dihydroxyethanol, 1,3-dihydroxyisopropanol and the like.

As used herein the term "$C_{1-C6}$ alkyl" refers to a saturated straight or branched chain hydrocarbon radical of from one to six carbon atoms. Included within the scope of this term are methyl, ethyl, n-propyl, isopropyl, n-butyl, isobutyl, tert-butyl, n-pentyl, n-hexyl and the like.

As used herein the term "$C_1$–$C_8$ alkyl" refers to a saturated straight or branched chain hydrocarbon radical of from one to eight carbon atoms. Included within the scope of this term are methyl, ethyl, n-propyl, isopropyl, n-butyl, isobutyl, tert-butyl, n-pentyl, n-hexyl, n-heptyl, n-octyl and the like.

As used herein, the term "$C_{1-4}$ alkanethiol" refers to a saturated straight or branched chain hydrocarbon radical of from one to four carbon atoms containing a thiol functional group. Included within the scope of this term are methylthiol, ethylthiol, propylthiol, isopropylthiol, n-butylthiol, isobutylthiol, t-butylthiol and the like.

As used herein, the term "acetylthioalkane" refers to a saturated straight or branched chain hydrocarbon radical of from one to eight carbon atoms containing an acetylthiol functional group. Included withing the scope of this term are acetylthiomethyl, acetylthioethyl, acetylthiopropyl, acetylthioisopropyl, acetylthio-butyl, acetylthio-s-butyl, acetylthio-t-butyl and the like.

As used herein, the term "$C_1$–$C_6$ alkanoyloxy" refers to a saturated straight or branched chain hydrocarbon radical of from one to eight carbon atoms containing a carboxylato functional group. Included with the scope of this term are formyloxy, acetoxy, propionyloxy, isopionyloxy, n-butyryloxy, s-butyryloxy, t-butyryloxy, n-pentanoyloxy, s-pentanoyloxy, t-pentanoy, n-hexanoyloxy and the like.

As used herein, the term "pharmaceutically acceptable salts" is readily determinable by one of ordinary skill in the art and means an acid addition salt which does not pose a significant toxic effect to the patient and which possesses desirable pharmaceutical handling and formulation properties. Such salts can be either inorganic or organic and may be hydrated or substantially anhydrous. Illustrative inorganic acids which form suitable salts include hydrochloric, hydrobromic, sulphuric, phosphoric acid and metal salts such as sodium monohydrogen orthophsphate and potassium hydrogen sulfate. Illustrative organic acids which form suitable salts include the mono, di and tri carboxylic acids. Illustrative of but not limited to such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, and sulfonic acids such as methane sulfonic acid and 2-hydroxybenzoic and 2-hydroxyethane sulfonic acid.

conditions, such as the number and types of substituents, the reaction time, the solvent and the temperature used. That said, general guidelines for the parameters of the formation of the thermodynamic dienolate intermediate via deprotonation at the steroid carbon 6 are illustrated in the following text. The range of usable "strong bases" include metal alcoholates and the like, but preferably are the salts of branched chain alcohols of 3 to 6 carbons. Most preferably, these branched chain alcohols contain 3 to 5 carbons. For example, potassium tert-butoxide.

The "effective amount" of strong base is variable depending upon the number of acidic protons on the steroid. An "acidic proton" is one which readily dissociates, for example, OH, $CO_2H$, NH. For each acidic proton an additional equivalent of base is used. Using the typical bases described herein and "non-acidic proton" containing steroids, the amount is at least two (2) molar equivalents relative to the steroidal compound. Preferably it is two to four molar equivalents, and most preferably it is about two (2) molar equivalents, exclusive of acidic protons.

In the creation of the dienolate intermediate in the nitration reaction, one of ordinary skill will recognize the sliding range between temperature and the time of the reaction. At elevated temperatures one would expect shorter reaction times, while at lower temperatures, longer reaction times. In the practice of the invention, an "elevated temperature" is between about 50° C. to about 100° C., preferably between 50° C. and 83° C., and a most preferred reaction temperature is about 83° C. At elevated temperatures, the "time sufficient to create the corresponding thermodynamic dienolate" is between about 15 minutes and 8 hours, preferably between about 15 minutes and about 180 minutes, and a most preferred reaction time is about 60 minutes.

At lower temperatures a "suitable temperature" ranges from about 15° C. to about 50° C., preferably 17° C. to about 30° C. and most preferably from about 20° C. to about 25° C. At these temperatures, the "time sufficient to create a thermodynamic dienolate" is between about 15 minutes and 48 hours, preferably about 1 hour to 24 hours, and most

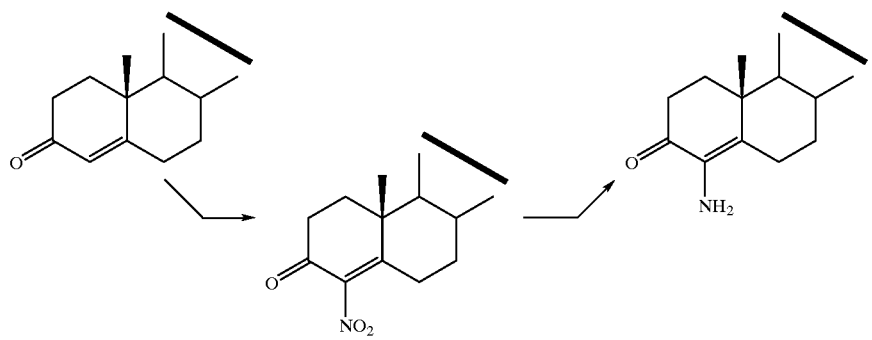

The above reaction scheme illustrates the process of the invention, wherein a $\Delta^4$-3-one steroid is nitrated to the corresponding 4-nitro compound first by reaction with an effective amount of a base sufficiently strong to generate the $\Delta^{3,5}$-dienolate. By "effective amount of a strong base," it is meant a base of strength and concentration suitable to convert the $\Delta^4$-3-one starting compound into its thermodynamic dienolate under suitable reaction conditions.

In the selection of suitable reaction conditions, the exact base and concentration thereof is a function of other reaction preferred about 10 to 24 hours. Reaction yields can be increased by using lower reaction temperatures with longer reaction times, and are preferred in the practice of the invention. Since certain solvents which are advantageously used with the process of the invention may have a freezing point at the lower end of above temperature range, it may be necessary to slightly warm and or mix the solvent with one of the reactants before the reaction can procede at these lower temperatures.

Solvents suitable to effect the nitration can be any alcohol derived from straight or brached chain alkanes containing from two (2) to five (5) carbon atoms. Particularly desirable are secondary and tertiary alcohols. For example, while ethanol or isopropanol may be used effectively, tert-amyl alcohol and tert-butyl alcohol are preferred. The most preferred solvent is tert-butanol.

The nitration can be effected by any neutral nitrating agent, for example, alkyl nitrates. The choice of a particular alkyl nitrate is determined by considerations of reactivity and cost. Suitable alkyl nitrates are any saturated straight or branched chain organo-nitrate containing from three to eight carbon atoms. Preferable alkyl nitrates include isopropyl nitrate, isobutyl nitrate and 2-ethyl hexylnitrate. The most preferred suitable alkyl nitrate is isopropyl nitrate.

The reduction of the 4-nitrosteroid compound by a suitable reducing agent may be effected by any known means, including, for example, either chemically or catalytically. Typical chemical catalysts include: 1) zinc metal in acetic acid; 2) zinc metal in methanol either in the presence or absence of ammonium chloride; 3) stannous chloride in ethanol; or 4) iron and acetic acid in ethanol. An effective catalytic system includes Lindlar's catalyst (palladium on calcium carbonate "poisoned" with lead and quinoline) in an alcohol solvent such as ethanol. Other systems may be used in the catalytic hydrogenation, for example palladium on charcoal and ammonium formate in methanol, palladium on charcoal and trifluoroacetic acid in ethanol, or palladium on barium sulfate in ethanol.

The in vitro enzymatic inhibitory activity of the present compounds as inhibitors of steroid $C_{17-20}$ lyase was established using microsomal preparations of the enzyme from rat or cynomolgus monkey testicular tissue. Microsomes were isolated from cynomolgus monkey or rat testicular tissue. The compound to be tested was dissolved in dimethyl sulfoxide and diluted in 0.05M potassium phosphate buffer, (pH 7.4 for cynomolgus monkey lyase activity and pH 7.2 for rat lyase activity) to give the desired concentrations of test compound. The final assay concentration of DMSO was 0.1% (v/v). Assays contained an NADPH regenerating system comprised of 1M NADPH, 5 mM glucose-6-phosphate, 1 IU/mL glucose-6-phosphate dehydrogenase and microsomal protein in a total volume of 0.2 mL.

For determination of time dependent $C_{17-20}$ lyase inactivation, the test compound was incubated with 20 to 62 µg/mL microsomal protein, 0.05 M potassium phosphate buffer, pH 7.4, and the NADPH regenerating system described above at 34° C. for 0 to 40 minutes. Aliquots of 180 µL were then removed and assayed for enzyme activity. Each aliquot was added to [7-$^3$H]-17α-hydroxypregnenolone (11.2 mCi/mmole; 0.2 µCi per assay) plus unlabeled 17α-hydroxypregnenolone to give a total substrate concentration of 0.3 µM per assay and subsequently incubated for 6 minutes at 34° C. For determination of reversible inhibition by the test compound, the reaction was initiated by the addition of substrate and inhibitor (or DMSO in buffer for controls) simultaneously to the other assay components. The substrate used for cynomolgus monkey lyase was 7-$^3$H-17α-hydroxypregnenolone, which yielded a final concentration of 0.3 µM substrate. For assay of rat lyase activity, the substrate used was [1,2-$^3$H]-17α-hydroxyprogesterone to give a total substrate concentration of 0.1 µM ($K_m$=0.095 µM). The complete assay was incubated at 34° C. for 6 minutes for both rat and monkey lyase.

The activity of the present compounds as inhibitors of steroid 5α-reductase was determined using microsomal preparations of the 5α-reductase enzyme from laboratory animal prostate tissue. Specifically, microsomes were isolated from cynomolgus monkey prostate tissue. Protein concentration of the microsomal preparations was determined prior to use of the samples. Individual assays of cynomolgus monkey prostatic 5α-reductase activity contained 0.1 M potassium phosphate-sodium citrate buffer, pH 5.6, 0.1% bovine serum albumin (w/v), 1.0 mM sodium EDTA, 7 to 96 mg of microsomal protein, 1.0 mM NADPH, 5.0 mM glucose-6-phosphate, 1 IU/mL glucose-6-phosphate dehydrogenase, [1,2-3H]-testosterone (0.15 µCi), unlabeled testosterone to yield the desired concentration of substrate, and inhibitor which was dissolved in DMSO then diluted in 0.1 M potassium-sodium citrate buffer (50:50), pH 5.6, to yield a final assay concentration of 0.1% (v/v) DMSO. The same buffer and DMSO without inhibitor were used in control assays. Background radioactivity was determined from assays containing all components except enzyme. Assays were performed in duplicate. The reaction was initiated by the addition of testosterone and incubated for 30 minutes at 25° C. in a Dubnoff® shaker incubator. The total volume of the assay was 100 µL. The assay was linear with time to 30 minutes under these conditions.

Compound to be tested for inhibition was added simultaneously with testosterone. For $IC_{50}$ determinations, a single concentration of testosterone at the $K_m$ level was used. The $K_m$ values of testosterone were determined in multiple experiments, and ranged from 0.025 µM to 0.091 µM for cynomolgus 5α-reductase.

Each assay was terminated by addition of 5 mL of chloroform:methanol (2:1). Carrier steroid (2.5 µg each) representing substrates and products and 0.8 mL of distilled, deionized water were then added to each assay. Carrier steroids for the lyase assays were 17α-hydroxypregnenolone, dehydroepiandrosterone, and androst-5-ene-3β,17β-diol (cynomolgus monkey lyase assays) or 17α-hydroxyprogesterone, androstenedione, and testosterone (rat lyase assays). Testosterone, dihydrotestosterone, and 3,17-androstanediol were added to the 5α-reductase assays as carrier steroids. Radiolabeled and unlabeled steroid were extracted by the method of Moore and Wilson (Methods in Enzymol., eds. O'Malley, B. W. and Hardlan, J. G. 36, 1975, pp. 466–473). The organic phase containing the steroids was evaporated using nitrogen gas. For lyase assays, the residues dissolved in 18% tetrahydrofuran (v/v) in hexane. For 5α-reductase assays, the dried steroid residues were dissolved in 3% (v/v) isopropanol in hexane. the steroids were then separated by normal phase HPLC on a LiCrosorb® DIOL derivatized silica gel column (10 µm; 4×250 mm) with a 3% to 7.5% isopropanol in hexane gradient, followed by isocratic conditions of 75% (v/v) isopropanol in hexane. Radioactivity in the steroid peaks was measured using a Radiomatic® Model HS or Model A515 Flo-One detector for both lyase and 5α-reductase assays.

The enzyme activity for each assay was calculated from the percent conversion of substrate to products, and the results were expressed as percent inhibition of control. The data from these experiments were fitted into the appropriate two parameter model incorporating six concentrations of inhibitor to determine an $IC_{50}$ value. When the compounds were tested using the above procedures, the following results were obtained: (20S)-20-hydroxymethyl-4-nitropregn-4-en-3-one exhibited an $IC_{50}$ of 41 nM for monkey testicular$C_{17-20}$ lyase, 86 nM for rat testicular $C_{17-20}$ lyase and 17 nM prostatic monkey 5α-reductase. When the compounds were tested using the above procedures with cynomolgus monkey testicular lyase, the following results were obtained:

| Compound | Preincubation Time | Concentration ($\mu M$) | % Inhibition |
|---|---|---|---|
| 17β-cyclopropyloxy-4-nitroandrost-4-en-3-one | 0 | 1 | 78 |
|  |  | 0.1 | 36 |
|  | 40 | 1 | 95 |
|  |  | 0.1 | 79 |
| (20S)-20-mercaptomethyl-4-nitropregn-4-en-3-one | 0 | 1 | 69 |
|  |  | 0.1 | 0 |
|  | 40 | 1 | 93 |
|  |  | 0.1 | 26 |

In the inhibition of steroid $C_{17-20}$ lyase, 5α-reductase and/or $C_{17\alpha}$-hydroxylase the "effective inhibitory amount" is such amount of compound wherein an enzyme inhibitory effect is achieved. The exact amount necessary to achieve the desired inhibitory level is a function of enzyme concentration, surface area, temperature and other typical experimental parameters, and is within experimental variation of one of ordinary skill in the art. Typically, when such compounds are administered to actual patients, the minimal effective amount is such amount where therapeutic effect is achieved. The exact amount of compound to be administered will vary over a wide range, depending principally upon patient type and size. For example, depending on the patient to be treated, and the severity of the condition being treated, the effective inhibitory amount of compound administered can vary from about 0.625 to 62.5 mg/kg of body weight per day and is preferably from about 0.5 to 30 mg/kg of body weight per day. Unit dosages for oral administration may contain, for example, from 10 to 500 mg of a compound of the invention. Alternatively, the present compounds can be administered by parenteral routes or by implants.

The following examples are presented to illustrate the present invention but they should not be construed as limiting it in any way. As used herein, unless described otherwise, all references to "room temperature" shall mean about 20° C. to about 23° C.

Step One: Preparation of 4-nitrosteroids

EXAMPLE 1

(20S)-20-Hydroxymethyl-4-nitropregn-4-en-3-one

Potassium tert-butoxide (1.70 g, 15 mM) and (20S)-20-hydroxymethylpregn-4-en-3-one (1.65 g, 5 mM) are mixed together in tert-butanol (25 mL), and heated at reflux temperature under argon atmosphere for 75 minutes. Isopropylnitrate (0.51 mL, 5 mM) is then added to the refluxing reaction mixture, resulting in an exothermic reaction. After one minute, the reaction vessel is removed from heat and allowed to cool to room temperature. The cooled mixture is then made acidic by addition of acetic acid (5 mL), and stirred overnight. The mixture is then diluted with dichloromethane so as to form a separate phase sufficient to solubilize the synthesized product. Subsequently, the solids are removed by filtration and washed with dichloromethane. The materials in both the filtrate and wash(es) are combined together and concentrated. The residue is then redissolved in dichloromethane, then purified by flash chromatagraphy on silica gel to give (20S)-20-hydroxymethyl-4-nitropregn-4-en3-one. The crystallization of this material from aqueous acetone gives white needles (m.p. 166–168° C.).

IR 3435, 1696, 1623(m), 1633 cm$^{-1}$

MS(CI) 376(100%, M+1), 358(30%, M+1-H$_2$O)

$^1$H-NMR (CDCl$_3$) δ0.73(3H, s, $C_{18}$—Me), 1.06(d, $C_{20}$—Me), 1.29(s, $C_{19}$—Me), 3.38(1H, dd, ½.$C_{21}$-CH$_2$), 3.64(1H, dd, ½.$C_{21}$—CH$_2$). Analysis. Calculated for $C_{22}H_{33}NO_4$·(0.2)H$_2$O: C, 69.70; H, 8.80; N, 3.62; Found: C, 69.78; H, 9.13; N, 3.40. This compound has the following structure:

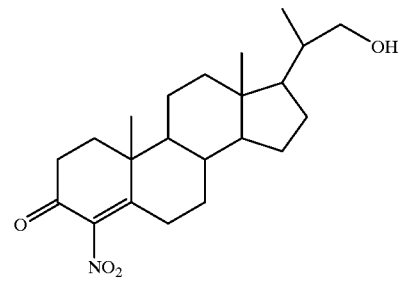

EXAMPLE 1A (20S)-20-hydroxymethyl-4-nitropregn-4-en-3-one

Potassium tert-butoxide (1.70 g, 15 mM), (20S)-20-hydroxymethylpregn-4-en-3-one (1.65 g, 5 mM) are mixed in tert-butanol and heated at reflux temperature, under argon atmosphere for 90 minutes. The combination is then cooled to room temperature and treated with one continuous portion of isopropylnitrate (0.51 mL, 5 mM). After 18 hours, the contents of the reaction vessel are acidified with 5 ml of acetic acid, and subsequently diluted with dichloromethane. The solids are then removed by filtration and further washed with additional dichloromethane. The filtrate and wash residue are purified as described in Example 1 to give a crystallized (20S)-20-hydroxymethyl-4-nitropregn-4-en-3-one.

EXAMPLE 1B (20S)-20-hydroxymethyl-4-nitropregn-4-en-3-one

Potassium tert-butoxide (1.70 g, 15 mM) and (20S)-20-hydroxymethylpregn-4-en-3 (1.65 g, 5 mM) are combined in tert-butanol (25 ml) and stirred at room temperature for 3 hours under an argon atmosphere. To the combination is then added, as one continuous portion, iso-propylnitrate (0.51 ml, 5 mM ) after which the combination is stirred overnight. Acetic acid (5 ml) is then added. After 1 hour, the solids remaining in the reaction vessel are filtered off and washed with dicloromethane. The combined filtrate and washing residue are then purified as described in Example 1 to give crystallized (20S)-20-hydroxymethyl-4-nitropregn-4-en-3-one.

EXAMPLE 1C (20S)-20-hydroxymethyl-4-nitropregn-4-en-3-one

Potassium tert-butoxide (7.6 g, 67.8 mM), (20S)-20-hydroxymethylpregn-4-en-3-one (6.6 g, 20 mM) in tert-butanol is heated at reflux temperature for 60 minutes under an argon atmosphere. Isobutylnitrate (2.34 ml, 20 mM) is then added in one continuous portion. After 20 minutes of further refluxing, the reaction vessel is cooled to room temperature. Acetic acid (10 ml) is then added, and the reaction vessel stirred for 18 hours, after which the combination is diluted with dichloromethane (200 mL). The solids are removed, washed, and recombined with the washing residue and subsequently purified as described in Example 1 to give crystallized (20S)-20-hydroxymethyl-4-nitropregn-4-en-3-one.

EXAMPLE 1D (20S)-20-hydroxymethyl-4-nitropregn-4-en-3-one

Potasium tert-butoxide (7.6 g, 67.8 mM) and (20S)-20-hydroxymethylpregn-4-en-3-one (6.6 g, 20 mM) are combined in tert-butanol and heated at reflux temperature for 120 minutes. 2-ethylhexylnitrate (3.56 ml, 20 mM) is then added in one continuous portion. After 10 minutes, the reaction vessel is cooled to room temperature. The reaction is then quenched with acetic acid (9 ml) and stirred overnight. After diluting with dichloromethane (200 mL), the solids are removed, washed, and combined with the washing residue and subsequently purified as described in Example 1 to give crystallized (20S)-20-hydroxymethyl-4-nitropregn-4-en-3-one.

EXAMPLE 1E (20S)-20-hydroxymethyl-4-nitropregn-4-en-3-one

React (20S)-Hydroxymethyl-pregn-4-en-3-one (6.18 g, 18.7 mmol) in tert-butanol (91 mL) with potassium tert-butoxide (6.43 g, 57.3 mmol, 3 molar equiv.) at reflux temperature for 1.5 hours. Add isopropyl nitrate (2.9 mL, 1.6 molar equiv.) dropwise over 20 minutes after which the reaction is allowed to cool to room temperature then stirred overnight (12–18 hours). The reaction mixture is then treated with acetic acid (6.2 mL), stirred for 1 hour at room temperature and poured into water (400 mL). Extract with dichloromethane (4×100 mL), combining all the organic phases which is dried over magnesium sulfate. After filtering, evaporate the filtrate in vacuo providing a reddish oil, which is purified by silica gel plug filtration (hexanes:Et$_2$O:CH$_2$Cl$_2$=4:2:1, 2.5 L then 2:2:1, 1 L). Combine and concentrate the appropriate fractions and recrystallize the resulting material from boiling isopropanol to which water is added until turbid to give the title compound (2.66 g).

EXAMPLE 2

17β-Hydroxy-4-nitroandrost-4-en-3-one

By the method of example 1, testosterone (2.88 g, 10 mM), potassium tert-butoxide (3.40 g, 30 mM) and isopropylnitrate (1.01 ml) are reacted to yield 17β-hydroxy-4-nitroandrost-4-en-3-one, m.p. 158–160° C. (acetone-hexane)

IR 3533, 1689, 1615(m), 1635 cm$^{-1}$

MS(CI) 334(100%, M+1), 316(50%, M+1-H$_2$O)

$^1$H-NMR δ (CDCl$_3$) 0.80(3H, s, C$_{18}$—Me), 1.30(s, C$_{19}$—Me), 3.66(1H, t, C$_{17}$.H). This compound has the following structure:

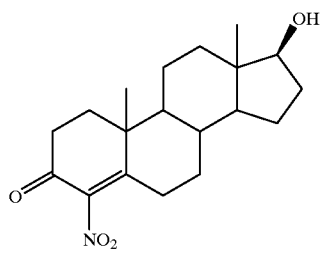

The combined filtrate and washes from the above crystallization can be treated with acetic anhydride (3 mL) and pyridine (6 mL). After standing overnight at room temperature, the reaction is stirred with water for 1 hour. A sticky solid is obtained by decantation of the liquids and then purified by chromatography to give 17β-acetoxy-4-nitroandrost-4-en-3-one, m.p. 216–217° C. (aqueous acetone).

IR (CHCl$_3$) 1725, 1695, 1623(m), 1536, 1256 cm$^{-1}$

MS(CI) 376(100%, M+1), 316(35%, M+1-AcOH)

$^1$H-NMR (CDCl$_3$) 0.84(3H, s, C$_{18}$—Me), 1.30(s, C$_{19}$—Me), 2.05(s, COMe), 5.62(1H, dd, C$_{17}$—H).

This compound has the following structure:

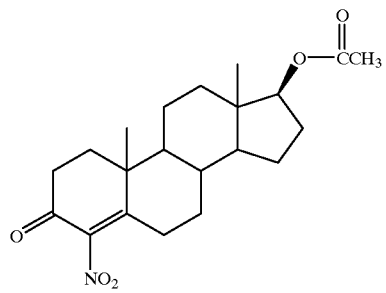

As suggested previously, the 17β-hydroxy-4-nitrosteroid may be modified into the corresponding 17-one, such as described in the following example.

EXAMPLE 2A 4-nitroandrost-4-ene-3,17-dione

A solution of 17β-hydroxy-4-nitroandrost-4-en-3-one (4-nitrotestosterone, 10.56 g, 31.7 mM) in acetone (900 ml) cooled to −6° C. is treated with Jones reagent (10.0 ml). After the excess reagent is decomposed with methanol, the solids are removed by filtration. The filtrate is concentrated, for example on a rotary evaporator under vaccum, then purified by flash chromatography on silica gel to give 4-nitroandrost-4-ene-3,17-dione, m.p. 205–205.5° C. dec. (acetone-hexane).

IR 1738, 1622, 1533, 1373 cm.$^{-1}$

MS(CI) 332(100%, M+1)

$^1$H-NMR(CDCl$_3$) 0.93(s, C$_{18}$—Me), 1.13(s, C$_{19}$—Me).

The compound has the following structure:

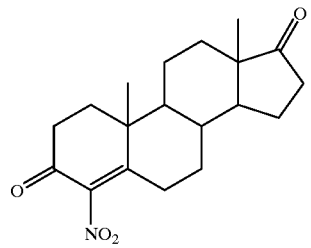

EXAMPLE 3

17β-hydroxy-7α-methyl-4-nitroandrost-4-en-3-one

17α-hydroxy-7α-methyltestosterone (11.2 g, 37.0 mM), potassium tert-butoxide (8.29 g, 73.9 mM) and isopropylnitrate (3.76 ml) are reacted by the method of example 1 to give 17β-hydroxy-7α-methyl-4-nitroandrost-4-en-3-one, m.p. 229–230° C. dec.(acetone-hexane).

IR (CHCl$_3$) 3614, 1694, 1658 (m), 1623, 1536 cm$^{-1}$

MS(CI) 348 (100%, M+1), 330 (40%, M+1-H$_2$O )

$^1$H-NMR (CDCl$_3$) 0.89 (d, C$_7$—Me), 0.91 (s, C$_{18}$—Me), 1.16 (s, C$_{19}$—Me), 3.68 (t, C$_{17}$—H).

The compound has the following structure:

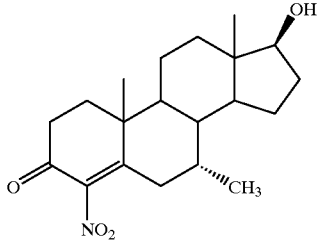

The 17β-hydroxysteroid may be converted into the corresponding 17-one by the procedure described in the following example.

EXAMPLE 3A

7α-methyl-4-nitroandrost-4-ene-3,17-dione

A solution of 17β-hydroxy-7α-methyl-4-nitroandrost-4-en-3-one (4.2 g, 12.1 mM) in acetone (400 ml) is cooled to 0° C. and is treated with Jones reagent (4.0 ml). Any excess reagent is decomposed by addition of methanol. The solids are filtered off and the filtrate is concentrated to a green solid. This material is purified by flash chromatography on silica gel to give 7α-methyl-4-nitroandrost-4-ene-3,17-dione (aqueous acetone).

IR (CHCl$_3$) 1735, 1697, 1625(m), 1537 cm$^{-1}$

MS(CI) 346(100%, M+1), 328(50%, M+1-H$_2$O)

$^1$H-NMR(CDCl$_3$) 0.86(3H, d, C$_7$—H), 0.93(3H, s, C$_{18}$—Me), 1.33(s, C$_{19}$—Me).

The compound has the following structure:

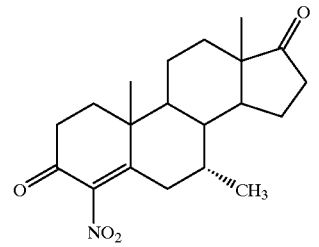

EXAMPLE 4

11α,17β-dihydroxy-17α-methyl-4-nitroandrost-4-en-3-one

11α,17β-dihydroxy-17α-methylandrost-4-en-3-one (6.37 g, 20.0 mM), potassium tert-butoxide (6.73 g., 60.0 mM) and iso-propyl nitrate (2.02 ml) are reacted by the method of Example 1 to yield 11α,17β-dihydroxy-17α-methyl-4-nitroandrost-4-en-3-one as a solid foam.

IR 3435, 1691, 1618(m), 1533, 1373 cm$^{-1}$

MS(CI) 364(100%, M+1), 346(30%, M+1-H$_2$O), 328 (37%, M+1-2H$_2$O)

$^1$H-NMR (CDCl$_3$) 0.93(3H, S, C$_{18}$—Me), 1.21(s, C$_{19}$—Me), 1.43 (s, C$_{17}$—Me), 4.08 (1H, dt, C$_{11}$—H).

The compound has the following structure:

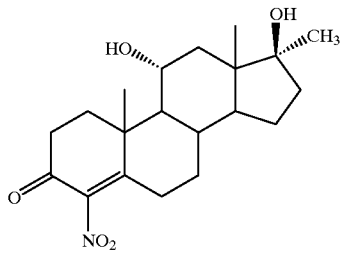

EXAMPLE 5

20,21-dihydroxy-4-nitropregn-4-en-3-one Acetonide 20,21-dihydroxypregn-4-en-3-one-21-acetate (6.73 g, 18.0 mM), potassium tert-butoxide (5.78 g., 51.5 mM) and isopropyl nitrate (1.60 ml) are reacted by the method of Example 1 to give 20,21-dihydroxy-4-nitropregn-4-en-3-one. Recrystallization from aqueous acetone yields the corresponding acetonide, m.p. 221–223° C. (dec).

IR 1693, 1622(m), 1535, 1371 m$^{-1}$

MS(CI) 418(55%, M+1), 101(100%)

$^1$H-NMR (CDCl$_3$) 0.90(3H, s, C$_{18}$.Me), 1.03(s, C$_{19}$—Me), 1.33 (s, Me), 1.37(s, Me), 3.46–3.54(1H, m, C$_{20}$—H), 3.93–4.05 (2H, m, C$_{21}$—CH$_2$).

The compound has the following structure:

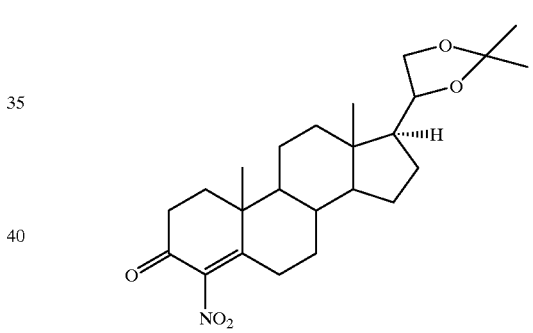

The acetonide group can be removed from the 20,21 dioxygenated carbons by the procedure of the following example.

EXAMPLE 5A 20,21-dihydroxy-4-nitropregn-4-en-3-one

A solution of 20,21-dihydroxy-4-nitropregn-4-en-3-one acetonide obtained from the recrystallization filtrate of Example 5 in methanol is briefly warmed to assist in forming a solution. The reaction vessel is then cooled to room temperature whereupon 5% aqueous hydrochloric acid (10 mL) is added. After 4 hours of stirring, the reaction is neutralized with aqueous potassium carbonate and concentrated in vacuo. The residue is partitioned between dilute aqueous hydrochloric acid and dichloromethane. The organic layer is then separated, dried over magnesium sulfate and concentrated to a yellow foam which is then purified by flash chromatography on silica gel to give 20,21-dihydroxy-4-nitro-pregn-4-en-3-one, m.p. 183–185° C. (aqueous methanol).

IR (CHCl$_3$) 3628, 3587, 1693, 1622, 1535, 1373 cm$^{-1}$

MS(CI) 378(100%, M+1), 342(35%, M+1-2H$_2$O)

$^1$H-NMR 0.92(3H, s, C$_{18}$—Me), 1.30(3H, s, C$_{19}$—Me), 3.34–3.44 (1H, m, C$_{20}$—H), 3.61–3.72(2H, m, C$_{21}$—CH$_2$).

The compound has the following structure:

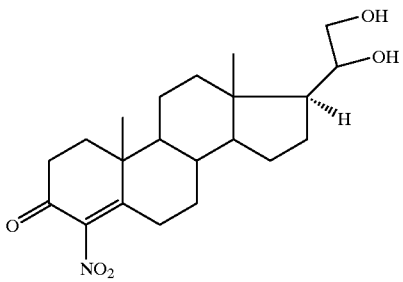

EXAMPLE 6

17β-cyclopropyloxy-4-nitroandrost-4-en-3-one

17β-cyclopropyloxy-androst-4-en-3-one (9.70 g, 29.5 mM), potassium tert-butoxide (7.0 g, 62.4 mM), and isopropyl nitrate (2.99 ml) are reacted by the method of Example 1 to yield 17β-cyclopropyloxy-4-nitroandrost-4-en-3-one, m.p. 137–38° C. (methanol)

IR (CHCl$_3$), 1695, 1622(m), 1535, 1373cm$^{-1}$

MS(CI) 374(100%, M+10, 316(20%, M+1-c-C$_3$H$_5$—O)

$^1$H-NMR (CDCl$_3$) 0.38–0.61(4H, m), 0.80(3H, s, C$_{18}$—Me), 1.29(s, C$_{19}$—Me), 3.25–3.33(1H, m, cyclopropyl-CHO), 3.44(1H, t, C$_{17}$—H).

The compound has the following structure:

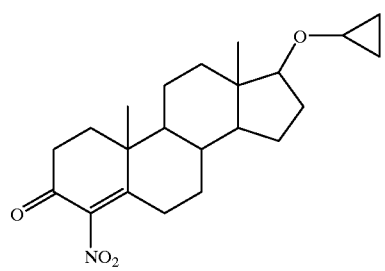

The starting material for the above nitration may be prepared as follows:

A solution of 17β-cyclopropyloxy-androst-5-en-3β-ol (19.36 g, 58.9 mM) in acetone (1.9 L) is cooled to −3° C. and then treated with Jones reagent (20 ml). The excess reagent is decomposed with methanol. The solids are removed by filtration. The filtrate is concentrated to a green oil which is purified by flash chromatography on silica gel to give 17β-cyclopropyloxy-androst-4-en-3-one (11.0 g, 57%).

The starting material (17β-cyclopropyloxy-androst-5-en-3β-ol) for the above oxidation may be prepared as described in U.S. Pat. No. 4,966,897 to Angelastro and Blohm.

EXAMPLE 6A

17β-(cyclopropoxy)-4-nitro-androst-4-en-3-one

Potassium tert-butoxide (109 g, 0.97 mol, 2.1 molar equivalents) is added to a stirred solution of 17β-(cyclopropyloxy)-androst-4-en-3-one (150 g, 0.46 mol) in tert-butanol (2 L) over 10 minutes at room temperature and under nitrogen. Continue stirring at room temperature for 18 hours, then add isopropylnitrate (48.2 g, 0.46 mol, 1.0 mol. equiv.) in tert-butanol (50 mL) over 30 minutes at room temperature. After an additional day of continuous stirring at room temperature, glacial acetic acid (130 mL) is added over 25 minutes and stirring is continued for an additional 18 hours. Subsequently, methylene chloride (1.5 L) and brine (saturated NaCl, 800 mL) is added and the solution is stirred an additional 10 minutes. The organic phase is then seperated and dried over magnesium sulfate. The resulting slurry is filered and the filtrate concentrated (35° C./40 Torr) to give a dark red oil. Purify by flash chromatography (SiO2, elution: EtOAc/hexane 5:95, EtOAc/hexane 1:9 and EtOAc/hexane 15:85). Combine and concentrate the fractions containing the desired product (30° C./40 Torr) to give a solid residue which is stirred under hexane (350 mL). Filter and dry the solids to give the title compound (68 g, 40%) as a yellow solid. Additional compound is obtained from the filtrate after concentration and rechromatography as above (8 g, 5%). mp 133–134° C.

IR (KBr) 3437, 3090, 2945, 2870, 1693, 1624, 1531, 1450, 1373, 1346, 1332, 1211, 1188, 1170, 1076, 1062, 1035, 1012, 962, 794, 765 cm$^{-1}$.

1H-NMR (CDC13) δ0.50 (4H, m, 2×cyclopropyl-CH2), 0.80(3H, s, C18-Me), 1.30(3H, s, C19-Me), 3.3(3H, m, OCH of cyclopropyl), 3.44(1H, t, C17-H).

MS (CI, CH4) m/z (rel. intensity) 374 (100%, M+1). Analysis calculated for C22H31NO4: C, 70.75; H, 8.37; N, 3.75; Found: C, 70.99; H, 8.44; N, 3.56.

EXAMPLE 7

4-nitro-androst-4-en-3-one-17β-carboxylic acid

Androst-4-en-3-one-17β-carboxylic acid (3.63 g, 11.4 mmol), potassium tert-butoxide (4 g, 35.3 mmol) and isopropylnitrate (1.9 mL) are reacted by the method of Example 1 to yield 4-nitro-21-androst-4-en-3-one-17β-carboxylic acid, m.p. 205–208° C. dec.

IR (CHCl$_3$) 3034, 2970, 1697, 1535, 1373 cm$^{-1}$

MS(CI) 362(100%, M+1)

$^1$H-NMR δ (CDCl$_3$) 0.79(3H, s, C$_{18}$.Me), 1.3(3H, s, C$_{19}$.Me).

The compound has the following structure:

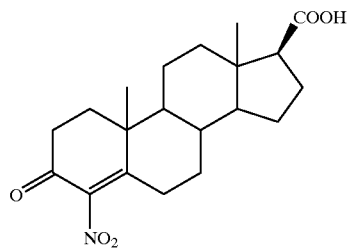

EXAMPLE 8

3-hydroxy-4-nitroandrost-3,5-diene-17β-tert-butyl carboxamide

To a 250 mL round bottom flask equipped with a magnetic stirring bar and a gas inlet was placed potassium tert-butoxide (8.5 g, 75 mmole) and tert-butyl alcohol (75 mL). Androst-4-ene-3-one-17β-carboxamide (9.3 g, 25 mmol) was added and the solution was stirred at 65° C. under an argon atmosphere for 20 minutes. Isopropyl nitrate (2.8 mL, 28 mmol) was added causing a strong exotherm and the solution was cooled to 25° C. over a 1 hour period. Acetic acid (7.5 mL) was added, the precipitate was filtered, and the filtrate was concentrated. The resulting dark gum was dissolved in dichloromethane, washed with water, concentrated, and chromatographed on 300 mL silica gel using 30–50% ethyl acetate/hexane to give 441 mg (1.05 mmol) of crystalline product from dichloromethane/hexane.

m.p. 207–208.5° C. (dec.); IR (KBr): 3441, 2967, 2943, 2916, 2885, 2847, 1693, 1670, 1624, 1535, 1508, 1475, 1452, 1390, 1367 cm$^{-1}$.

UV (EtOH) $\lambda_{max}$=242 nM; $\epsilon$=13,100;

$^{1}$H-NMR (CDCl3): δ4.40 (s, 1H), 2.52–2.60 (m, 2H), 1.4–2.46 (m, 16H), 1.35 (s, 9H), 1.31 (s, 3H), 1.03–1.32 (m, 4H), 0.74 (s, 3H) ppm;

Analysis calc'd for $C_{24}H_{36}N_2O_4$: C: 69.20%; H: 8.71%, N: 6.72%; Found C: 69.33%, H: 8.63%, N:6.60%.

The compound has the following structure:

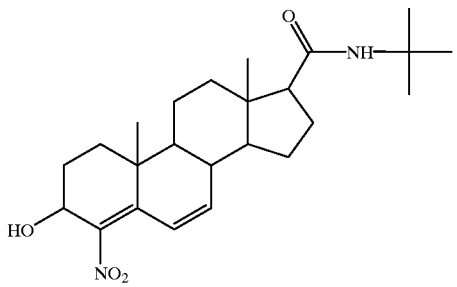

EXAMPLE 9A 20-acetylthiomethyl-4-nitropregn-4-en-3-one

A solution of 20-hydroxymethyl-4-nitropregn-4-en-3-one (750 mg, 2.0 mmol)(prepared in Example 1) and tosyl chloride (400 mg, 2.1 mmol) was prepared in pyridine (2 ml) and stirred at 25° C. for 12 hours. After 24 hours, the residue was redissolved in dichloromethane (2 ml) and additional tosyl chloride (40 mg) added. After stirring another 12 hours, 2 drops H$_2$O were added and the mixture was stirred for 30 minutes and washed with dichloromethane (50 ml), water (50 ml), 10% HCl (50 ml) and dried over MgSO$_4$. This material was concentrated and crystallized from a 50:50 solution of ethyl acetate:hexane (1:1) to give a yellow solid. m.p. 181° C.–182° C.

The tosylate (529 mg) prepared by the above procedure was dissolved in dry dimethylformamide (10 ml) and added to CsSCOCH$_3$ newly prepared by dissolving Cs$_2$CO$_3$ (163 mg, 0.5 mmol) and HSCOCH$_3$ (86 mg, 1.1 mmol) in CH$_3$OH (3 mL) and evaporating. After 24 hours, the reaction was diluted with diethyl ether, washed with water, concentrated and flash chromatographed using dichloromethane/hexane (4:1). The fractions containing the desired product were concentrated and crystallized from hexane to give 225 mg thioester.

Alternatively, the tosylate prepared by the above procedure was displaced to make the corresponding thioacetyl compound by the following procedure: CS$_2$CO$_3$ (163 mg, 0.5 mmol) was dissolved in methanol (2 mL) and HSCOCH$_3$ (90 mg, 1.1 mmol). The homogenous solution was concentrated in vacuo. The remaining residue was dissolved in dimethyl formamide (3 mL) with the tosylate (529 mg, 1.0 mmol). The resulting solution was stirred at 25° C. under N$_2$ for 18 hours. Another solution (1.0 mL of dimethylformamide) of cesium thioacetate (1.0 mmol) prepared in the above manner was added to the reaction vessel. Upon completion of the conversion (determined by TLC), 1N HCl (1 mL) was added and the resulting solution was dissolved in ethyl acetate, washed in water and dried over magnesium sulfate.

The compound has the following structure:

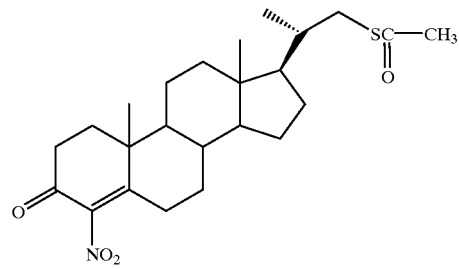

EXAMPLE 9B 20-mercaptomethyl-4-nitropregn-4-en-3-one

The thioacetate prepared in Example 9A (65 mg, 0.15 mmol) was dissolved in 2 mL methanol and 1 mL THF with 0.3 mL of 1N LiOH. After stirring for 1 hour, 0.1 mL of acetic acid was added. The solution was extracted into ethyl acetate, washed with water and dried over magnesium sulfate. The product was dissolved into 1.0 ml acetic acid, heated to about 50° C. and concentrated in vacuo to give a light yellow solid (30 mg).

The compound had the following structure:

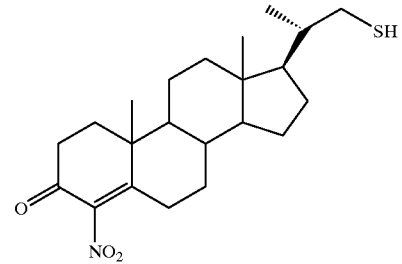

EXAMPLE 10

17β-cyclopropylamino-4-nitroandrost-4-en-3-one

A solution of 17β-cyclopropylamino-4-en-3-one (4.61 g, 14.07 mmol) and potassium tert-butoxide (4.74 g, 42.22 mmol, 3 molar equivalents) in tert-butanol (60 mL) was heated at reflux for 1 hour. Isopropyl nitrate (1.43 mL, 14.07 mmol, 1 molar equivalent) was added all at once as the solution was refluxing. The reaction was slowly cooled to room temperature, after which glacial acetic acid (20 mL) and dichloromethane (20 mL) was added to the reaction mixture to dissolve the red-orange precipitate. The reaction was allowed to stand at room temperature overnight. The reaction mixture was filtered and the filter cake washed with dichloromethane until white. The filtrate was diluted with additional dichloromethane (200 mL) and subsequently washed with an aqueous sodium chloride solution at one-half the saturated concentration (200 mL) followed by a washing of a solution consisting of equal parts aqueous half saturated sodium chloride and aqueous saturated sodium bicarbonate (200 mL). The organic layer was dried over magnesium sulfate and concentrated in vacuo and purified by chromatography on silica gel (dichloromethane/ methanol, 19:1) to give 17β-cyclopropylamino-4-nitroandrost-4-en-3-one as a solid yellow foam.

$^1$H-NMR (300 MHz, CDCl3) δ0.75(s, 3H, $C_{19}$—Me); 1.30 (s, 3H, $C_{18}$—Me) ppm.

IR(KBr) 3435, 2944, 2870, 1695, 1533, 1371, 1013, 766 cm$^{-1}$.

MS(EI)=372 (M+).

The compound has the following structure:

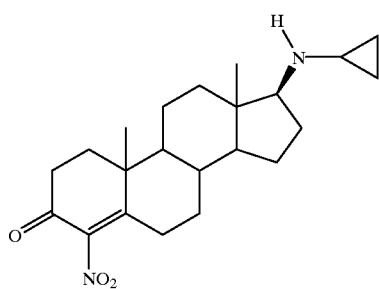

Step Two: Reduction of Steroidal 4-nitro-$\Delta^4$-3-ones into 4-amino-$\Delta^4$-3-one Steroidal Compounds A. Catalytic Reduction

EXAMPLE 11

4-amino-20-hydroxymethylpregn-4-en-3-one

A solution of 20-hydroxymethyl-4-nitropregn-4-en-3-one (2.01 g, 5.35 mM) in absolute ethanol (28 mL) is treated sequentially with Lindlar's catalyst (5% Pd on $CaCO_3$ with 5.2% Pb, 0.81 g) and with quinoline (37 μl) and kept under hydrogen at between 40–55 p.s.i. for 24 hours. The mixture is then filtered through celite, and the filtrate is concentrated to a yellow solid which is purified by short path chromatography to give 4-amino-20-hydroxymethylpregn-4-en-3-one, m.p. 180–185° C. (aqueous isopropanol).

IR 3512, 3470, 3384, 1648, 1614, 1576 cm$^{-1}$

MS(CI) 346(100%, M+1), 328(30%, M+1-$H_2O$).

$^1$H-NMR 0.72(3H, s, $C_8$—Me), 1.02(d, $C_{21}$—Me), 1.15(s, $C_{19}$—Me), 2.6–3.2 (v.br, $NH_2$), 3.36(1H, dd, $0.5.C_{22}$—$CH_2$), 3.63(1H, dd, $0.5C_{22}$—$CH_2$). The compound has the following structure:

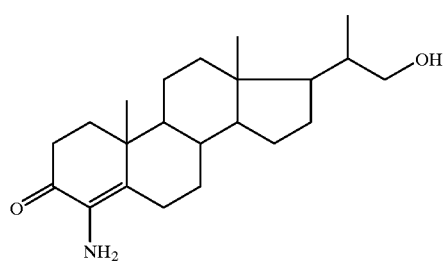

EXAMPLE 12

17β-cyclopropyloxy-4-amino-androst-4-en-3-one

A solution of 17β-cyclopropyloxy-4-nitroandrost-4-en-3-one (4.36 g, 11.6 mM) in absolute ethanol (125 mL) was treated with Lindlar's catalyst and then quinoline (80 mL). The mixture was stirred under hydrogen at 1 atmosphere pressure for about 117 hours. The reaction mixture was filtered through celite topped with charcoal and washed with absolute ethanol. The combined filtrate and wash was concentrated to a brown liquid (3.7 g) and dissolved in methylene chloride, placed atop a column of silica gel prepared with hexane/ethyl acetate (1:4) and purified by flash chromatography and eluting in hexane:ethyl acetate (1:4).

The product containing fractions were combined and concentrated to yield a light yellow glass which crystallized on standing (2.3 g). The crystals were dissolved in methanol, filtered through cotton, and water was added dropwise until crystallization began. The mixture was refrigerated overnight (12–18 hours). The crystals were collected by filtration and washed with cold aqueous methanol and with water, then dried in vacuo to give 4-amino-17β-(cyclopropyloxy)-androst-4-en-3-one as a light yellow solid (1.97 g).

IR(KBr) v3458, 3372, 1674, 1622 (m), 1585 cm$^{-1}$.

Anal. calc'd for $C_{22}H_{33}NO_2$: C: 76.92; H: 9.68; N: 4.08. Found: C: 76.86; H: 10.04; N: 4.08.

$^1$H-NMR (CDCl$_3$) δ0.38–0.61 (4H, m, 2×$CH_2$), 0.79 (3H, s, $C_{18}$—Me), 1.15 (s,$C_{19}$—Me), 3.27+3.44+ca.3.4 (4H, cyclproxy-H, $C_{17}$—H, $NH_2$, m+t, v.br.).

UV(EtOH) λ 294(ε 7570, 1 g.ε 3.879)

MS/CI 344(100%, M+1), 286(30%, M+1-$C_3H_5OH$). The compound has the following structure;

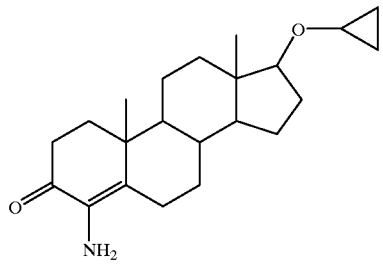

EXAMPLE 12A 4-amino-17β-(cyclopropoxy)-androst-4-en-3-one hydrochloride

To a stirred solution of 17β-(cyclopropyloxy)-4-nitroandrost-4-en-3-one (10 g, 26.7 mmol) in methanol (200 mL) at 35° C. was added Lindlar's catalyst (4 g, 5.9% Pd+5.4% Pb/CCP3 ($CaCO_3$), D. R. Engelhard, Seneca, S.C.) and quinoline (0.2 g, 1.6 mmol) under a nitrogen atmosphere. The resulting mixture was placed in a Parr shaker and shaken under a hydrogen atmosphere at room temperature under 50 psi for 20 hours, whereupon about 3 molar equivalents of hydrogen were consumed. The catalyst was removed by filtration.

The above procedure was repeated about 9 times (8×10 g-scale and 1×7-g scale), and the product solutions after filtration were combined. Silicon dioxide ($SiO_2$, 550 g) was added to the solution and the mixture was concentrated under reduced pressure (10 Torr) and temperature (10–15° C.). The mixture of $SiO_2$ and product was loaded onto a flash column (20 cm i.d., containing 5 kg of $SiO_2$) and the column was eluted sequentially with 15% (20 L), 20% (20 L) and 30% (40 L) of ethyl acetate in hexane. The product containing fractions were pooled and concentrated at reduced temperature (10° C. and pressure (30 Torr) to give a yellow solution (600 mL). The solution was treated with 1.8 M HCl in ethyl acetate (75 mL) at 4° C. The resulting slurry was diluted with acetone (200 mL) and CH$_2$Cl$_2$ (100 mL). After stirring for 30 minutes, the solids were collected by filtration and washed with acetone (300 mL) and dried to give the title compound (34 g, 37%); mp 206–207° C. The filtrate was concentrated to a solution (300 mL) and the solid was collected to give a second crop of compound (3.4 g, 4%); mp 203–204° C.

IR (KBr) 3445, 3086, 2945, 2872, 2555, 1967, 1791, 1682, 1641 cm$^{-1}$.

$^1$H-NMR (CDCl$_3$) δ0.50(4H, m, 2×cyclopropyl-CH$_2$), 0.76(3H, s, C$_{18}$—Me), 1.21(3H, s, C$_{19}$—CH$_3$), 3.2 (1H, m, OCH of cyclopropyl), 3.39 (1H, t, C$_{17}$—H), 9.6 (3H, br.s, NH$_3$).

MS (CI) m/z 344 (100%, M$^+$).

Anal. calc'd for C$_{22}$H$_{34}$NO$_2$Cl.(0.6)H$_2$O: C, 68.05; H, 9.07; N, 3.61. Found C, 68.18; H, 9.06; N, 3.52.

EXAMPLE 13

17β-cyclopropylamino-4-aminopregn-4-en-3-one

17β-cyclopropylamino-4-nitropregn-4-en-3-one (670 mg, 1.80 mmol) was dissolved in absolute ethanol (11 mL) and treated with Lindlar catalyst (268 mg) followed by quinoline (3 μL). The solution was stirred vigorously under a hydrogen atmosphere at atmospheric pressure (about 760 mm/mg) for 18 hours. The reaction mixture was filtered and washed with ethanol (100 mL) and dichloromethane (100 mL). The solvents were removed in vacuo and the product purified by chromatagraph on silica gel (CH$_2$Cl$_2$/CH$_2$OH, 47:3) to give a yellow oil which crystallized to a yellowish solid. m.p. 149–150° C. (Et$_2$O).

IR(KBr): 3474, 3366, 2945, 1616, 1577 cm$^{-1}$

MS(Cl/CH4) [M$^+$+H]=343

$^1$H-NMR (33 MHz, CDCl$_3$) δ60.73(3H, s, C$_{18}$—Me), 1.15(3H, s, C$_{19}$—Me), 2.66 (1H, t, C$_{17}$—H)

$^{13}$C-NMR (75 MHz, CDCl$_3$) δ6.464, 7.185, 11.289, 20.803, 23.682, 24.757, 29.683, 29.753, 30.914, 32.860, 34.899, 35.307, 37.904, 42.453, 52.910, 54.549, 69.014, 132.938, 138.860, 194.343.

The compound has the following structure:

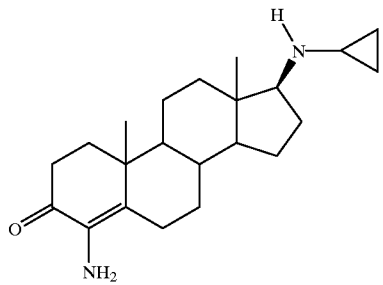

B. Chemical Reduction

EXAMPLE 14

4-amino-20-hydroxymethylpregn-4-en-3-one

A solution of 20-hydroxymethyl-4-nitropregn-4-en-3-one (0.52 g, 1.38 ml) in absolute ethanol (4.8 mL) is combined with stannous chloride (2.1 g) added in one portion and then heated to 70° C. for 6 hours. The reaction vessel is then cooled to room temperature and the solution is carefully neutralized with sodium bicarbonate (9 g) over a 10 minute period. The resulting slurry is then filtered, removing a brown solid which is then stirred in 10% hydrofluoric acid (25 mL) and ethyl acetate (25 mL). The HF/EtOAc treatment is repeated. The organic phases from each filtration are combined, dried over magnesium sulphate, filtered and concentrated. The resulting residue is purified by flash chromatagraphy to give 4-amino-20-hydroxymethylpregn-4-en-3-one as a white solid identical to the material described in U.S. Pat. No. 5,218,110 to Weintraub and U.S. Pat. No. 5,120,840 to Weintraub et al., which are both herein incorporated by reference. The compound has the following formula:

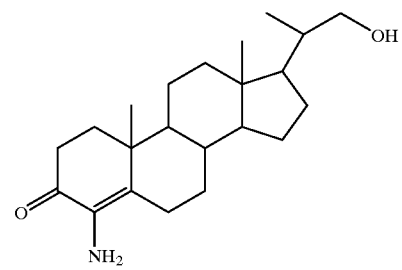

EXAMPLE 14

4-amino-17-cyclopropyloxyandrost-4-en-3-one

A solution of 17-cyclopropyloxy-4-nitroandrost-4-en-3-one (1.0 g, 2.71 mM) in acetic acid (10 mL) is treated with zinc dust (1.0 g). The combination is vigorously stirred for 1.5 hours at room temperature. The zinc salts are removed by filtration and washed with ethyl acetate. The combined filtrate and wash are combined and concentrated to a yellow solid which is then redissolved in ethyl acetate and extracted three times with 1M hydrochloric acid (150 ml). The combined acid extracts are neutralized with sodium hydroxide (pH 14) and further extracted with ether. The combined organic layers are then dried over sodium sulfate and concentrated to give 4-amino-17-cyclopropyloxyandrost-4-en-3-one (0.59 g), m.p. 100–102° C. (aqueous methanol).

IR 3354, 1662, 1620, 1581 cm$^{-1}$

MS(CI) 344(100%, M+1)

$^1$H-NMR 0.37–0.61(4H, m, 2×cyclopropyl CH$_2$), 0.79 (3H, s, C$_{18}$—Me), 1.16(s, C$_{19}$—Me), 3.25–3.33(m, cyclopropyl-CHO), 3.44(t, C$_{17}$—H).

The compound has the following structure:

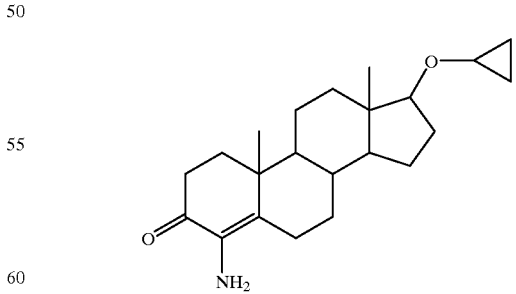

EXAMPLE 16

20-acetylthiomethyl-4-aminopregn-4-en-3-one 20-(Thioacetyl)methyl-4-nitropregn-4-en-3-one (173 mg, 0.40 mmol) and 300 mg zinc dust were stirred in 2 mL glacial acetic acid for 30 minutes. The mixture was poured into ethyl acetate (50 mL), washed with 3×50 mL of a saturated aqueous solution of sodium bicarbonate and dried over magnesium sulfate. m.p. 173° C.–176° C.

The compound had the following structure:

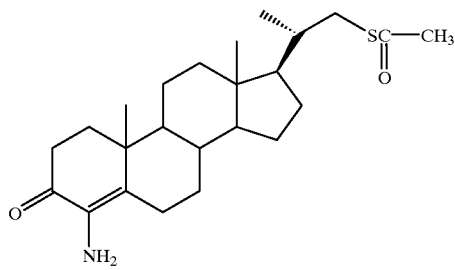

What is claimed is:

1. A process for preparing a compound of the formula:

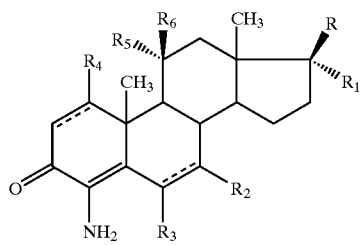

wherein

R is OH, $C_1$–$C_6$ alkanoyl, $C_1$–$C_6$ alkanoyloxy, $C_1$–$C_4$ alkanol, $COCH_2OH$, $CO_2H$, $CONR_7R_8$, cyclopropyloxy, acetylthioalkane, cyclopropylamino, t-butylcarboxamide, 2,2-dimethyldioxolan-4-yl, 1,2-dihydroxyethyl and $C_{1-4}$ alkanethiol;

$R_1$ is hydrogen, hydroxy or $C_{1-6}$ alkyl;

$R_2$, $R_3$ and $R_4$ are each independently hydrogen or $C_1$–$C_6$ alkyl;

$R_5$ and $R_6$ are each independently hydrogen or OH;

$R_7$ is hydrogen or $C_1$–$C_8$ alkyl;

$R_8$ is $C_1$–$C_8$ alkyl; and the notation ---- on the ring indicates that the bond may be a single or double bond;

wherein R and $R_1$ together, and/or $R_5$ and $R_6$ together may indicate =O;

with the proviso that when R is OH, then $R_1$ is hydrogen; and with the proviso that, when $R_5$ is OH, then $R_6$ is hydrogen;

comprising sequentially:

a) reacting a starting compound of the formula:

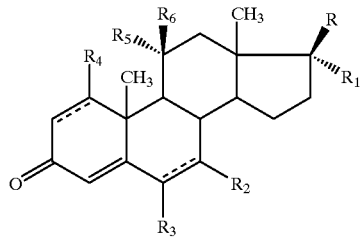

wherein R–$R_8$, and ---- are defined as above, with an effective amount of a strong base, at an elevated temperature for a time sufficient to create the corresponding thermodynamic 3,5-dienolate, followed by addition of a neutral nitrating agent to produce a 4-nitrosteroid; and then b) reacting the 4-nitrosteroid with a suitable reducing agent.

2. The process of claim 1 wherein the compound is (17S)-cyclopropyloxy-androst-4-en-3-one.

3. The process of claim 1 wherein the compound is is (20S)-4amino-21-hydroxy-20-methylpregn-4-en-3-one.

4. The process of claim 1 wherein the strong base is selected from the group comprising potassium tert-butoxide and potassium tert-amylate.

5. The process of claim 4 wherein the effective amount of strong base is between about two and about four molar equivalents.

6. The process of claim 5 wherein the effective amount of strong base is about two molar equivalents.

7. The process of claim 1 wherein the elevated temperature is between about 17° C. and about 100° C.

8. The process of claim 7 wherein the elevated temperature is between about 50° C. and about 83° C.

9. The process of claim 8 wherein the elevated temperature is about 83° C.

10. The process of claim 1 wherein the period of time sufficient to create the thermodynamic dienolate is between about 5 minutes and 8 hours.

11. The process of claim 10 wherein the period of time sufficient to create the thermodynamic dienolate is between about 15 minutes and about 180 minutes.

12. The process of claim 11 wherein the period of time sufficient to create the thermodynamic dienolate is about 60 minutes.

13. The process of claim 1 wherein the neutral nitrating agent is an alkyl nitrate which is a saturated straight or branched chain organo-nitrate containing from three to eight carbon atoms.

14. The process of claim 13 wherein the alkyl nitrate is selected from the group comprising isopropyl nitrate, isobuytl nitrate and 2-ethyl hexylnitrate.

15. The process of claim 14 wherein the suitable reducing agent is selected from the group comprising: a zinc metal in acetic acid; or zinc metal in methanol, or Lindlar's catalyst.

16. A process for preparing a compound of the formula:

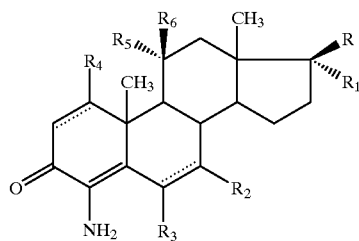

wherein

R is OH, $C_1$–$C_6$ alkanoyl, $C_1$–$C_6$ alkanoyloxy, $C_1$–$C_4$ alkanol, $COCH_2OH$, $CO_2H$, $CONR_7R_8$, cyclopropyloxy, acetylthioalkane, cyclopropylamino, tert-butylcarboxamide, 2,2-dimethyldioxolan-4-yl, 1,2-dihydroxyethyl and $C_{1-4}$ alkanethiol;

$R_1$ is hydrogen, hydroxy or $C_{1-6}$ alkyl;

$R_2$, $R_3$ and $R_4$ are each independently hydrogen or $C_1$–$C_6$ alkyl;

$R_5$ and $R_6$ are each independently hydrogen or OH;

$R_7$ is hydrogen or $C_1$–$C_8$ alkyl;

$R_8$ is $C_1$–$C_8$ alkyl; and the notation ---- on the ring indicates that the bond may be a single or double bond;

wherein R and $R_1$ together, and/or $R_5$ and $R_6$ together may indicate =O;

with the proviso that when R is OH, then $R_1$ is hydrogen or $C_{1-4}$ alkyl; and with the proviso that, when $R_5$ is OH, then $R_6$ is hydrogen and when $R^6$ is OH, then $R^5$ is hydrogen;

comprising sequentially:

a) reacting a starting compound of the formula:

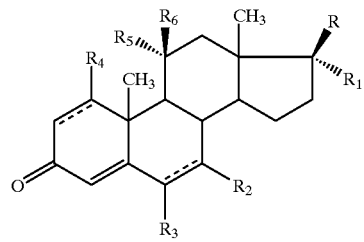

I wherein R–$R_8$, and ---- are defined as above, with an effective amount of a strong base, at a suitable temperature for a time sufficient to create the corresponding thermodynamic 3,5-dienolate, followed by addition of a neutral nitrating agent to produce a 4-nitrosteroid; and then b) reacting the 4-nitrosteroid with a suitable reducing agent; and c) optionally converting into a pharmaceutically acceptable salt.

17. The process of claim 16 wherein the compound is (17S)-4-amino-cyclopropyloxy-androst-4-en-3-one.

18. The process of claim 16 wherein the compound is (20S)-4amino-21-hydroxy-20-methylpregn-4-en-3-one.

19. The process of claim 16 wherein the compound is 4-amino-21-hydroxy-20-methylpregn-4-en-3-one hydrochloride.

20. The process of claim 18 wherein the suitable temperature is between about 17° C. to about 30° C.

21. The process of claim 16 wherein the suitable temperature is between about 20° C. to about 25° C.

* * * * *